(12) United States Patent
Duffy et al.

(10) Patent No.: US 10,927,071 B2
(45) Date of Patent: Feb. 23, 2021

(54) PROCESS FOR PREPARING ELECTRON DEFICIENT OLEFINS

(71) Applicant: Henkel IP & Holding GmbH, Duesseldorf (DE)

(72) Inventors: Cormac Duffy, Dundalk (IE); Marisa Phelan, Roscrea (IE); Barry Burns, Dublin (IE)

(73) Assignee: Henkel IP & Holding GmbH, Duesseldorf (DE)

( * ) Notice: Subject to any disclaimer, the term of this patent is extended or adjusted under 35 U.S.C. 154(b) by 0 days.

(21) Appl. No.: 16/438,540

(22) Filed: Jun. 12, 2019

(65) Prior Publication Data

US 2019/0292141 A1   Sep. 26, 2019

Related U.S. Application Data

(63) Continuation of application No. PCT/EP2017/082351, filed on Dec. 12, 2017.

(30) Foreign Application Priority Data

Dec. 23, 2016 (GB) .................................... 1622107

(51) Int. Cl.
| | | |
|---|---|---|
| C07C 253/30 | (2006.01) | |
| C07C 255/23 | (2006.01) | |
| B01J 23/20 | (2006.01) | |
| B01J 27/12 | (2006.01) | |
| B01J 23/10 | (2006.01) | |
| B01J 31/22 | (2006.01) | |

(52) U.S. Cl.
CPC ............ C07C 253/30 (2013.01); B01J 23/10 (2013.01); B01J 23/20 (2013.01); B01J 27/12 (2013.01); B01J 31/2256 (2013.01); C07C 255/23 (2013.01); B01J 2231/342 (2013.01); B01J 2231/349 (2013.01); B01J 2531/38 (2013.01)

(58) Field of Classification Search
CPC ..................... C07C 253/30; C07C 255/23
See application file for complete search history.

(56) References Cited

U.S. PATENT DOCUMENTS

| | | |
|---|---|---|
| 2,756,251 A | 7/1956 | Joyner et al. |
| 2,763,677 A | 9/1956 | Jeremias |
| 3,142,698 A | 7/1964 | Halpern et al. |
| 3,654,340 A | 4/1972 | Banitt |
| 3,728,375 A | 4/1973 | Coover, Jr. et al. |
| 3,903,055 A | 9/1975 | Buck |
| 3,975,422 A | 8/1976 | Buck |
| 4,003,942 A | 1/1977 | Buck |
| 4,012,402 A | 3/1977 | Buck |
| 4,013,703 A | 3/1977 | Buck |
| 4,202,920 A | 5/1980 | Renner et al. |
| 4,364,876 A | 12/1982 | Kimura et al. |
| 4,512,357 A | 4/1985 | Earl |
| 4,587,059 A | 5/1986 | Harth et al. |
| 5,386,047 A | 1/1995 | Nakos et al. |
| 2,721,858 A | 10/1995 | Joyner et al. |
| 5,455,369 A | 10/1995 | Meier et al. |
| 5,624,699 A | 4/1997 | Lang |
| 5,703,267 A | 12/1997 | Takahashi et al. |
| 6,096,848 A | 8/2000 | Gololobov et al. |
| 6,245,933 B1 | 6/2001 | Malofsky et al. |
| 6,436,866 B1 | 8/2002 | Nishikido et al. |
| 7,569,719 B1 | 8/2009 | McArdle et al. |
| 7,659,423 B1 | 2/2010 | McArdle |
| 7,718,821 B1 | 5/2010 | Bigi et al. |
| 8,022,251 B2 | 9/2011 | McArdle et al. |
| 8,053,589 B1 | 11/2011 | McArdle et al. |
| 8,329,936 B2 | 12/2012 | Friese et al. |
| 8,481,755 B2 | 7/2013 | McArdle et al. |
| 8,686,105 B2 | 4/2014 | McArdle et al. |
| 2012/0023021 A1 | 1/2012 | Seifert et al. |

FOREIGN PATENT DOCUMENTS

| | | |
|---|---|---|
| CN | 103922964 A | 7/2014 |
| DE | 2738285 A1 | 3/1979 |
| EP | 0459617 A1 | 12/1991 |
| JP | 2012106982 A | 6/2012 |
| WO | 2015004566 A2 | 1/2015 |
| WO | 2015150882 A1 | 10/2015 |

OTHER PUBLICATIONS

Ilangovan, A.; Muralidharan, S. and Maruthamuthu, S. "A Systematic Study on Knoevenagel Reaction and Nazarov Cyclization of Less Reactive Carbonyl Compounds Using Rare Earth Triflates and Its Applications." Journal of the Korean Chemical Society, vol. 55, No. 6, 2011.

Wen-Bun, Y. et al. "Ytterbium Perfluorooctanesulfonate-Catalyzed Knoevenagel Condensation in Fluorous Biphasic System", Organic Preparations and Procedures International, vol. 39, No. 1, 2007, pp. 71-75.

Narsaiah, A. et al. "An Efficient Knoevenagel Condensation Catalyzed by LaCl3. H2O in Heterogenous Medium." Synthetic communications, vol. 33, No. 21, 2003, pp. 3825-3832.

Remme, N. et al. "Scandium Triflate Catalyzed Transesterification of Carboxylic Esters", Synlett, vol. 20007, No. 3, 2007, pp. 491-493.

Fu, X. et al. "Transesterification catalyzed by samarium tri-2-propoxide", Chinese Journal of Chemistry, vol. 15, No. 1, 1997, pp. 90-93.

Vijayalakshmi, V. et al. "Alkyl and substituted alkyl 2-cyanoacrylates. Part 1. Synthesis and properities" J. Adhesion Sci. Technol., vol. 4, No. 9, 1990, pp. 733-750.

Guseva, T. I. et al. "Organic Chemistry: Synthesis of functionally substituted cyanoacetates" Russian Chemical Bulletin, vol. 42, No. 3, Mar. 1993, pp. 478-480.

(Continued)

*Primary Examiner* — Shawquia Jackson
(74) *Attorney, Agent, or Firm* — Steven C. Bauman

(57) ABSTRACT

This invention relates to a process for producing electron deficient olefins, such as 2-cyanoacrylates, using an acid catalyzed Knoevenagel condensation reaction.

18 Claims, 1 Drawing Sheet

(56) References Cited

OTHER PUBLICATIONS

Guseva, T. I. et al. "Organic Chemistry: Synthesis of functionally substituted 2-cyanoacrylates" Russian Chemical Bulletin, vol. 43, No. 4, Apr. 1994, pp. 595-598.

Barrett, A. G. and Braddock, D. C. "Scandium (III) or lanthanide (III) triflates as recyclable catalysts for the direct acetylation of alcohols with acetic acid." Chemical Communications, No. 4, 1997, pp. 351-352.

Gololobov, Y. G. et al. "2-Cyanoacrylates. Synthesis, properties and applications" Russian Chemical Reviews, 66 (11), 1997, pp. 953-962.

Senchenya, N. G. et al. "Silicon-containing esters of α-cyanoacrylic acid: synthesis and properties" Russian Chemical Bulletin, vol. 42, No. 5 May 1993, pp. 909-911.

Renner, A. et al. "Cure of Epoxy Resins with Esters of Cyanoacetic Acid" Journal of Polymer Science: Polymer Chemistry Edition, vol. 23, 1985, pp. 2341-2359.

Buck, Carl J. "Unequivocal Synthesis of Bis(2-Cyannoacrylate) Monomers, I. Via Anthracene Adducts" Journal of Polymer Science, Polymer Chemistry Edition, vol. 16, 1978, pp. 2475-2507.

Leelavathi, P. and Ramesh Kumar, S. "Niobium (V) chloride catalyzed Knoevenagel condensation: An efficient protocol for the preparation of electrophilic alkenes" Journal of Molecular Catalysis A: Chemical 240 (2005) pp. 99-102.

Ogiwara, Y. et al. "Indium(III)-Catalyzed Knoevenagel Condensation of Aldehydes and Activated Methylenes Using Acetic Anhydride as a Promoter" J. Org. Chem., 2015, 80, pp. 3101-3110.

Dawar, P. et al."One-Pot Esterification and Amide Formation via Acid-Catalyzed Dehydration and Ritter Reactions", Synthetic Communications, 2014, 44, pp. 836-846.

Opanasenko, M. "Catalytic behavior of metal-organic frameworks and zeolites: Rationalization and comparative analysis" Catalysis Today, 243, 2015, pp. 2-9.

Bartoli, G. et al. "Highly Efficient Solvent-Free Condensation of Carboxylic Acids with Alcohols Catalysed by Zinc Perchlorate Hexahydrate, Zn(ClO4)2•6H20" Adv. Synth. Catal., 2005, 347, pp. 33-38.

Almasi, M. et al. "Ce(III) and Lu(III) metal—organic frameworks with Lewis acid metalsites: Preparation, sorption properties and catalytic activity inKnoevenagel condensation" Catalysis Today 243, 2015, pp. 184-194.

Viswanadham, B. et al. "The Role of Copper Exchanged Phosphomolybdic Acid Catalyst for Knoevenagel Condensation" Catal. Lett. vol. 146, 2016, pp. 1470-1477.

Cativiela, C. et al. "Synthesis and Preparative Resolution of the trans-Cyclohexane Analogues of Phenylalanine" Eur. J. Org. Chem, 2004, pp. 3898-3908.

Dharma Rao, G. B. And Kaushik, M. P. "Efficient trans-acetoacylation mediated by ytterbium(III) triflate as a catalyst under solvent-free condition." Tetrahedron Letters 52 (2011) pp. 5104-5106.

Lakshmi Kantam, M. et al. "Transesterification of ß-keto esters catalyzed by transition metal complexes in a novel heterogeneous way." Catalysis Letters 62 (1999) pp. 67-69.

Magens, S. et al. "A Nucleophilic Fe Catalyst for Transesterifications under Neutral Conditions." Organic Letters, 2008, vol. 10, No. 1, pp. 53-56.

De Sairre, M.I. et al. "Niobium(V) oxide: a new and efficient catalyst for the transesterification of ß-keto esters." Tetrahedron Letters 46 (2005) pp. 2705-2708.

Seebach, Dieter. "Diisopropyl (2S,3S)-2,3-O-Isopropylidenetartrate", Organic Syntheses., vol. 65, Jan. 1987, p. 230, XP055445562, ISSN: 0078-6209, DOI: 10.15227/orgsyn.065.0230.

Shantha, K. L. et al. "Developments and applications of cyanoacrylate adhesives." J. Adhesion Sci. Technol. vol. 3, No. 4, 1989, pp. 237-260.

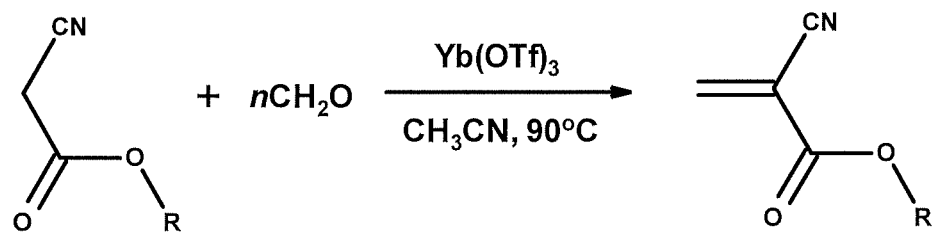

PROCESS FOR PREPARING ELECTRON DEFICIENT OLEFINS

BACKGROUND

Field

This invention relates to a process for preparing electron deficient olefins, such as 2-cyanoacrylates, using an acid catalyzed Knoevenagel condensation reaction.

Brief Description of Related Technology

Cyanoacrylate adhesives are known for their fast adhesion and ability to bond a wide variety of substrates. They are marketed as "super glue" type adhesives. They are useful as an all-purpose adhesive since they are a single component adhesive, very economical as only a small amount will do, and generally do not require any equipment to effectuate curing. Traditionally, cyanoacrylate monomers have been produced by way of a Knoevenagel condensation reaction between a formaldehyde precursor, such as paraformaldehyde, and an alkyl cyanoacetate under base catalysed conditions. During the reaction, cyanoacrylate monomer forms but, due to the prevailing basic reaction conditions, polymerises in situ to a prepolymer. The prepolymer is subsequently thermally cracked or depolymerised, yielding cyanoacrylate monomer. This approach has remained essentially the same over time, though various improvements and variants have been introduced. See e.g. U.S. Pat. Nos. 6,245,933, 5,624,699, 4,364,876, 2,721,858, 2,763,677 and 2,756,251.

The types of ester side chains that can be introduced to the cyanoacrylic acid ester both in terms of functionality and size is ordinarily limited when a basic catalyst is used in the synthetic steps, largely due to the thermal cracking step that follows in an attempt to liberate a cyanoacrylate monomer. Therefore a synthetic route which avoids the use of a basic catalyst and thermal cracking step is desirable and from a process perspective would be more cost-effective.

In U.S. Pat. No. 3,142,698, the synthesis of difunctional cyanoacrylates using a Knoevenagel condensation reaction is described. However, the ability to thermally depolymerise the resulting, now crosslinked, prepolymer in a reliable and reproducible manner to produce pure difunctional monomers in high yields is questionable [see J. Buck, *J. Polym. Sci., Polym. Chem. Ed.*, 16, 2475-2507 (1978), and U.S. Pat. Nos. 3,975,422, 3,903,055, 4,003,942, 4,012,402, and 4,013,703]. A variety of other processes for producing cyanoacrylate monomers are known, and some of which are described below.

U.S. Pat. No. 5,703,267 defines a process for producing a 2-cyanoacrylic acid which comprises subjecting a 2-cyanoacrylate and an organic acid (such as formic acid, acetic acid, propionic acid and butyric acid) to a transesterification reaction. Other organic acids are noted for use in the reaction as well: aromatic acids (specifically benzoic acid and phthalic acid), other fatty acids (specifically isobutyric acid, valeric acid, trimethylacetic acid, caproic acid, n-hexanoic acid, 2-methyl-pentanoic acid, n-octanoic acid, n-decanoic acid, lauric acid, palmitic acid, stearic acid, and oleic acid), derivatives of acetic acid (specifically fluoroacetic acid, chloroacetic acid, bromoacetic acid, iodoacetic acid, dichloroacetic acid, trichloroacetic acid, cyanoacetic acid, and vinylacetic acid), chloropropionic acid, and acrylic acid and methacrylic acid.

U.S. Pat. No. 5,455,369 defines an improvement in a process for preparing methyl cyanoacrylate, in which methyl cyanoacetate is reacted with formaldehyde to form a polymer that is then depolymerized to the monomeric product, and in which the purity of yield is 96% or better. The improvement of the '369 patent is reported to be conducting the process in a poly(ethylene glycol) diacetate, dipropionate, or dibutyrate, having a number average molecular weight of 200-400, as the solvent.

U.S. Pat. No. 6,096,848 defines a process for the production of a biscyanoacrylate, which comprises the steps of esterifying a 2-cyanoacrylic acid or transesterifying an alkyl ester thereof to obtain a reaction mixture; and fractionally crystallizing the reaction mixture to obtain the biscyanoacrylate.

U.S. Pat. No. 4,587,059 defines a process for the preparation of monomeric 2-cyanoacrylates comprising the steps of (a) reacting (i) a 2,4-dicyanoglutarate with (ii) formaldehyde, cyclic or linear polymers of formaldehyde, or a mixture thereof, in the presence of between about 0.5 and about 5 mols of water per mol of 2,4-dicyanoglutarate, at an acid pH of about 3 to slightly less than 7, and at a temperature of about 70 to about 140, to form an oligomeric intermediate product, and (b) removing water that is present from step (a) and thermolyzing the oligomeric intermediate product for a period of time sufficient to effect its conversion to monomeric 2-cyanoacrylates.

U.S. Pat. No. 3,654,340 (Banitt) describes and claims an added step in the condensation reaction of formaldehyde with esters of 2-cyanoacetic acid to produce 2-cyanoacrylate esters. The '340 patent focuses on catalyzing the reaction with a mixture of an acid and the salt of a primary or secondary amine with the same or stronger acid. The acid/amine combination is reported to reduce the extent of polymerization; however, polymerization still occurs and thus a thermal cracking step is required. The catalytic mixture is said to have a pH value of 5 or less when exact amounts of its components are dissolved in 25 ml of water. The '340 patent describes the process to be effective with fluorinated 2-cyanoacrylate esters.

U.S. Pat. No. 3,728,375 is directed to and claims monomeric α-cyanoacrylate esters having esters of an alkyl group of 1-16 carbon atoms, a cyclohexyl group, a phenyl group, an alkoxyalkyl group of 2-16 carbon atoms, a haloalkyl group of 1-10 carbon atoms, an alkenyl group of 2-16 carbon atoms, an arylalkyl group of 7-16 carbon atoms, or an acetoethyl group, and methods of forming the monomeric α-cyanoacrylate esters. Compositions made with these monomeric α-cyanoacrylate esters are prepared containing less than 200 ppm of water.

Recently, a series of U.S. patents have been granted that describe and claim the use of ionic liquids and/or iminium salts in an alternative synthesis of electron deficient olefins. See e.g. U.S. Pat. Nos. 7,659,423; 7,718,821; 7,569,719; 8,022,251; 8,053,589; and 8,686,105.

In addition, International Patent Publication No. WO2015/150882 A1 describes a process for preparing 1,1-disubstituted ethylene monomers (such as cyanoacrylates) using a catalytic amount of an ammonium or iminium salt in homogeneous phase or supported on a solid substrate. The process is reported to be a direct synthesis of such monomers, which does not require a cracking or thermal depolymerization step.

Nonetheless, commercial production of cyanoacrylate monomers ordinarily relies on the depolymerisation of a prepolymer formed under base-catalyzed Knoevenagel condensation reaction conditions, as noted above. Still today the Knoevenagel condensation reaction is believed to remain the most efficient and prevalent commercial method for producing high yields of monofunctional cyanoacrylates.

It would be desirable to not have to resort to thermally induced depolymerisation of a prepolymer produced by the Knoevenagel condensation reaction, for many of the reasons stated above. This prospect may also enable facile access to highly useful difunctional monomers, such as so-called biscyanaocrylates or hybrid materials of cyanoacrylate and other polymerizable or reactive functionality. The technical literature is replete with references to acid-catalyzed Knoevenagel condensation reactions, some of which even using lanthanide series elements, such as ybterrium. For instance, reference may be made to *J. Molec. Cat. A: Chemical*, 240, 99-102 (2005); *J. Org. Chem.*, 80, 3101-10 (2015); and *J. Kor. Chem. Soc.*, Vol. 55, No. 6, 1000-1006 (2011).

Nonetheless, apart from the '340 patent, absent from the published literature is the use of acid catalysts for the Knoevenagel condensation reaction in the preparation of 2-cyanoacrylates. Until now.

SUMMARY

Unlike the state of the technology, the present invention provides a direct or "crackless" synthesis of electron deficient olefins, specifically 2-cyanoacrylate monomers, using catalysts of either lanthanide elements or transition elements.

By employing an acid catalyst in the Knoevenagel reaction, thermal depolymerization or cracking can be avoided, thereby affording a direct synthesis to a cyanoacrylate monomer. Avoidance of this thermal depolymerization or cracking step offers greater opportunity to access electron deficient olefins, such as novel cyanoacrylates, which would otherwise be unobtainable through the conventional base-catalyzed Knoevenagel reaction/depolymerization process. Cost efficiencies may also be realized by the herein described acid-catalyzed Knoevenagel synthetic route to the existing range of monomers synthesized by the conventional Knoevenagel reaction.

The process for the preparation of a reactive electron deficient olefin is provided herein. In one, more focused, aspect, the invention includes the steps of:

(a) reacting a cyanoacetate and a source of aldehyde in the presence of a catalyst comprising a lanthanide element or a transition element, under appropriate conditions and for a time sufficient to yield a cyanoacrylate;

(b) optionally, separating from the mixture the so formed cyanoacrylate substantially free from the cyanoacetate, the source of aldehyde and/or the catalyst, and by-products.

In another, more broad, aspect, the invention provides a process for the preparation of a reactive electron deficient olefin that includes the steps of:

(a) reacting an electron deficient olefin precursor embraced by:

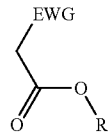

where EWG represents an electron withdrawing group, such as cyano or nitrile, alkoxy or aryloxy (which may itself be substituted by an EWG in the ortho and/or para position on the aromatic ring), carboxyl (e.g., carboxylic acids or carboxylic esters), sulphonic acids, carbonyls, halogens (e.g., F, Cl, Br, and I), nitro, isocyanate, sulfoxide and phosphine oxide; and R here represents straight chain, branched, cyclic or fused $C_{1-20}$ alkyl or alkylenyl, $C_{2-20}$ alkenyl or alkenylenyl, $C_{2-20}$ alkynyl or alkylenyl, and $C_{6-20}$ aryl or arylenyl or $C_{7-20}$ alkaryl or alkarylenyl, with or without substitution or interruption by one or more heteroatoms; and a source of aldehyde, in the presence of a catalyst comprising a lanthanide element or a transition element, under appropriate conditions and for a time sufficient to yield an electron deficient olefin;

(b) optionally, separating from the mixture the so formed electron deficient olefin substantially free from the cyanoacetate, the source of aldehyde and/or the catalyst, and by-products.

BRIEF DESCRIPTION OF THE FIGURE

FIG. 1 depicts a synthetic scheme according to the present invention. More specifically, FIG. 1 shows the reaction of a cyanoacetate with a formaldehyde source in an acetonitrile solvent at a temperature of 90° C. in the presence of ytterbium trifluoromethane sulfonate [Yb(OTf)$_3$]. The reaction generates the target cyanoacrylate. In the FIGURE, R represents straight chain, branched, cyclic or fused $C_{1-20}$ alkyl or alkylenyl, $C_{2-20}$ alkenyl or alkenylenyl, $C_{2-20}$ alkynyl or alkynylenyl, and $C_{6-20}$ aryl or arylenyl or $C_{7-20}$ alkaryl or alkarylenyl, with or without substitution or interruption by one or more heteroatoms.

DETAILED DESCRIPTION

As noted above, the present invention provides a process for the preparation of a reactive electron deficient olefin. In one, more focused, aspect, the invention includes the steps of:

(a) reacting a cyanoacetate and a source of aldehyde, in the presence of a catalyst comprising a lanthanide element or a transition element, under appropriate conditions and for a time sufficient to yield a cyanoacrylate;

(b) optionally, separating from the mixture the so formed cyanoacrylate substantially free from the cyanoacetate, the source of aldehyde and/or the catalyst, and by-products.

In another, more broad, aspect, the invention provides a process for the preparation of a reactive electron deficient olefin that includes the steps of:

(a) reacting the electron deficient olefin precursor embraced by:

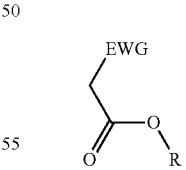

where EWG represents an electron withdrawing group, such as cyano or nitrile, alkoxy or aryloxy (which may itself be substituted by an EWG in the ortho and/or para position on the aromatic ring), carboxyl (e.g., carboxylic acids or carboxylic esters), sulphonic acids, carbonyls, halogens (e.g., F, Cl, Br, and I), nitro, isocyanate, sulfoxide and phosphine oxide; and R here represents straight chain, branched, cyclic or fused $C_{1-20}$ alkyl or alkylenyl, $C_{2-20}$ alkenyl or alkenylenyl, $C_{2-20}$ alkynyl or alkynylenyl, and $C_{6-20}$ aryl or arylenyl or $C_{7-20}$ alkaryl or alkarylenyl, with or without substitution or interruption by one or more heteroatoms; and a source of aldehyde; in the presence of a catalyst comprising a lanthanide element or a transition element, under appropriate conditions and for a time sufficient to yield an electron deficient olefin;

(b) optionally, separating from the mixture the so formed electron deficient olefin substantially free from the cyanoacetate, the source of aldehyde and/or the catalyst, and by-products.

By the processes of the present invention yields greater than 50%, desirably 60% and more desirably 70% may be achieved.

Reference to FIG. 1 may be useful to appreciate further the present invention, which is described in more detail below and in the Examples section that follows.

Thus, as an initial reactant in the inventive processes is a source of aldehyde. The aldehyde source may be aldehyde compounds having the structure R—CH=O, where R is hydrogen or vinyl. The aldehyde compound may be an aldehyde itself or a source of an aldehyde, such as one that yields an aldehyde like formaldehyde under reaction conditions. The aldehyde compound in a desirable embodiment includes formaldehyde (or a source thereof, such as paraformaldehyde), formalin, 1,3,5-trioxane, methylene diacetate, dimethoxymethane, or vinyl aldehydes, such as acrolein.

The source of aldehyde should be used in an amount of 1.0-2.0 equivalents, such as 2.0 equivalents.

As a reactant with such an aldehyde is an electron deficient olefin precursor (or, a 2-electron withdrawing group-substituted methylene compound).

The electron deficient olefin precursor is embraced by:

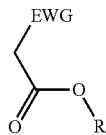

where EWG represents an electron withdrawing group, such as cyano or nitrile, alkoxy or aryloxy (which may itself be substituted by an EWG in the ortho and/or para position on the aromatic ring), carboxyl (e.g., carboxylic acids or carboxylic esters), sulphonic acids, carbonyls, halogens (e.g., F, Cl, Br, and I), nitro, isocyanate, sulfoxide and phosphine oxide; and R here represents straight chain, branched, cyclic or fused $C_{1-20}$ alkyl or alkylenyl, $C_{2-20}$ alkenyl or alkenylenyl, $C_{2-20}$ alkynyl or alkynylenyl, and $C_{6-20}$ aryl or arylenyl or $C_{7-20}$ alkaryl or alkarylenyl, with or without substitution or interruption by one or more heteroatoms.

This electron deficient olefin precursor contains a methylene linkage having at least one electron withdrawing substituent attached thereto, where the electron withdrawing substituent is selected from cyano or nitrile, alkoxy or aryloxy, carboxyl (such as carboxylic acids and carboxylic esters), sulphonic acids, carbonyls, halogens (e.g., F, Cl, Br, and I), nitro, isocyanate, sulfoxide and phosphine oxide.

Representative examples of these electron deficient olefin precursor compounds include malononitrile, malonic acid esters, malonoyl dihalides (e.g., malonoyl dichloride), ethyl nitroacetate, cyanoacetic acid esters (i.e., cyanoacetate), glycolic acid esters, 4-cyclopentene-1,3-dione, cyclopentane-1,3-dione, 4-cyclohexene-1,3-dione, cyclohexane-1,3-dione, 2,2-dimethyl-1,3-dioxane-4,6-dione (Meldrum's acid), and tetronic acid, some of which are commercially available for instance from Aldrich Chemical Co. A particularly desirable example is cyanoacetate.

The catalyst is acidic in nature, as measured or determined by its ability to donate a hydrogen (proton or hydrogen ion $H^+$), or, alternatively, its ability to form a covalent bond with an electron pair. To the lanthanide element or the transition element is bonded, coordinated or complexed, as appropriate, one or more ligands. The ligands may be selected for instance from conventional leaving groups used in organic synthetic schemes. Halogens, tosylates, mesylates, nitrates and triflates are chief among ligands that are suitable for use herein.

A prime example of a lanthanide element suitable for use in this connection is ytterbium, though others may also be useful, such as lanthanum, cerium, samarium, europium, and dysprosium. Prime examples of a transition element suitable for use in this connection are niobium, zirconium or scandium, with niobium being particularly desirable in this regard.

Desirable catalysts for use in the inventive process include ytterbium trifluoromethane sulfonate [Yb(OTf)$_3$] and niobium halides, such as niobium chloride.

The catalyst should be used in an amount of 0-20 mol %, such as 0.5-10 mol %, desirably 1-5 mol %, based on the electron deficient olefin precursor.

The electron deficient olefin so formed by the inventive processes may be a variety of olefins having at least one electron withdrawing group attached thereto.

In a desirable embodiment, the electron deficient olefin so formed will have two or more electron withdrawing groups attached thereto, which may be the same or different. For instance, the electron deficient olefin may be a compound having one end terminating with a cyanoacrylate, cyanopentadienoate, cyanohexadienoate, or alkylene derived from dimalonate and another end terminating with a group selected from branched and unbranched alkyl esters, esters containing aromatics and heterocyclic nuclei, (meth)acrylates, cyanoacrylates, siloxanes, blocked and unblocked isocyanates, anhydrides, silanes, vinyls, acetylenes, and epoxies.

Particularly desirable products have two electron withdrawing groups attached thereto which are different, such as 2-cyanoacrylate esters.

Representative examples of 2-cyanoacrylates so formed by the inventive processes include those having ester groups of methyl, ethyl, propyl, isoamyl, propargyl, butyl, pentyl, hexyl, octyl, nonyl, oxononyl, decyl, dodecyl, allyl, ethynyl, butenyl, cyclohexyl, phenyl, phenethyl, tetrahydrofurfuryl, chloroethyl, 2,2,2-trifluoroethyl, hexafluoroisopropyl, methoxymethyl, thiomethoxymethyl, methoxyethyl, thiomethoxyethyl, methoxybutyl, thiomethoxybutyl, ethoxyethyl, thioethoxyethyl, propoxyethyl, thioproxyethyl, butoxymethyl, thiobutoxymethyl, butoxyethyl, thiobutoxyethyl and dimethyl siloxane esters of 2-cyanoacrylic acid. This recitation is by no means however exhaustive.

The electron deficient olefin may also be a biscyanoacrylate, biscyanopentadienoate, biscyanohexadienoate, or a bis-alkylene derived from dimalonates or malononitrile, or combinations thereof.

The reaction of the inventive processes proceeds in solvent either forming a solution or a suspension. Acetonitrile has been used. In addition, different solvents may be used, such as benzonitrile, nitromethane, chlorobenzene, tetrachloroethene, toluene, THF, 1,4-dioxane, and (poly)ethylene glycol dialkyl ethers or esters. Ionic liquids may also be used as a solvent. The reaction of the inventive processes may proceed with or without heating or cooling, depending of course on the specific reactants and the scale of the reaction.

Decomposition of the source of aldehyde, e.g., paraformaldehyde, may occur under gentle heating up to a temperature of 70° C., to liberate formaldehyde in situ in the reaction medium. The temperature may be reached through an external heating element or internally by means of an exotherm that may be generated depending on the identity of the reactants. The temperature of the reaction should be controlled however to accommodate any such exothermic processes.

The time of reaction may be monitored by reference to the formation of the desired electron deficient olefin product. $^1$H NMR spectrometer is a particularly useful tool in this regard. The time of reaction may be as little as 30 minutes, for instance, or longer or shorter for that matter depending again on the identity of the specific reactants, the scale of the reaction and whether heat is added to the reaction conditions.

Once formed, the electron deficient olefin may be isolated as a product by removing solvent and then subsequently distilling away water formed as a by-product.

The electron deficient olefin so formed by the inventive processes may be stabilized during the synthesis and/or isolation procedure, and also in the isolated product to improve its shelf life. Suitable stabilizers include free radical stabilizers and acidic stabilizers, particularly in the case of 2-cyanoacrylate esters formed as the product of such inventive processes.

For example, free radical stabilizers include hydroquinone, pyrocatechol, resorcinol or derivatives thereof, such as hydroquinone monoethyl ether, or phenols, such as di-t-butylphenol or 2,6-di-t-butyl-p-cresol, 2,2'-methylene-bis-(4-methyl-6-t-butylphenol), bisphenol A, dihydroxydiphenylmethane, and styrenized phenols.

For example, acidic stabilizers include Lewis acids, sulfuric acid, hydrochloric acid, sulfonic acids, such as methane, ethane or higher sulfonic acids, p-toluene sulfonic acid, phosphoric acid or polyphosphoric acids, silyl esters of strong acids, such as those derived from trialkyl chlorosilanes, dialkyl dichlorosilanes, alkyl trichlorosilanes, tetrachlorosilane, trialkyl silylsulfonic acids, trialkyl silyl-p-toluene sulfonates, bis-trialkyl silylsulfate and trialkyl silylphosphoric acid esters.

The amount of stabilizer(s) used to stabilize the electron deficient olefin prepared by the inventive processes is well known to those of ordinary skill in the art, and may be varied depending on the properties of the resulting composition made from the so formed electron deficient olefin.

The following examples are intended to illustrate but in no way limit the present invention.

EXAMPLES

Example 1

To a 25 ml round bottomed flask was added 1.80 g (60 mmol) of paraformaldehyde, 3.39 g (30 mmol) of ethyl cyanoacetate and 10 mL of acetonitrile. The flask was fitted with a reflux condenser and magnetic stirrer before being immersed in an oil bath at a temperature of 90° C. The mixture was stirred at this temperature for a period of time of 30 minutes before a solution of 1.86 g (3 mmol, 10 mol %) ytterbium triflate in 5 mL of acetonitrile was added. The reaction was stopped at 23 hours. The relative conversion of cyanoacetate to cyanoacrylate was monitored by 500 MHz $^1$H NMR.

Relative Conversion by NMR: 17 hr: 55.59%
19 hr: 60.98%
21 hr: 66.58%
23 hr: 70.67%

Example 2

To a 25 ml round bottomed flask was added 1.80 g (60 mmol) of paraformaldehyde, 3.39 g (30 mmol) of ethyl cyanoacetate and 10 mL of nitromethane. The flask was fitted with a reflux condenser and magnetic stirrer before being immersed in an oil bath at a temperature of 105° C. The mixture was stirred at this temperature for a period of time of 30 min before a solution of 1.86 g (3 mmol, 10 mol %) ytterbium triflate in 5 mL of acetonitrile was added. The reaction was stopped at the 8 hour mark, where the relative conversion of cyanoacetate to cyanoacrylate by 500 MHz $^1$H NMR was determined to be 67.29%.

Example 3

To a 25 ml round bottomed flask was added 1.80 g (60 mmol) of paraformaldehyde, 6.699 g (30 mmol) of t-butyl-cyclohexyl-cyanoacetate and 10 mL of acetonitrile. The flask was fitted with a reflux condenser and magnetic stirrer before being immersed in an oil bath at 90° C. The mixture was stirred at this temperature for a period of time of 30 minutes before a solution of 1.86 g (3 mmol, 10 mol %) ytterbium triflate in 5 mL of acetonitrile was added. The reaction was stopped at 23 hours, where the relative conversion of cyanoacetate to cyanoacrylate by 500 MHz $^1$H NMR was determined to be 76.00%.

What is claimed is:

1. A process for the preparation of a reactive electron deficient olefin, steps of which comprise:
   (a) reacting a cyanoacetate and a source of aldehyde, in the presence of a catalyst comprising a lanthanide element or a transition element selected from the group consisting of niobium, zirconium or scandium, under appropriate conditions and for a time sufficient to yield a cyanoacrylate;
   (b) optionally, separating therefrom the so formed cyanoacrylate substantially free from the cyanoacetate, the source of aldehyde and/or the catalyst, and by-products.

2. A process for the preparation of a reactive electron deficient olefin, steps of which comprise:
   (a) reacting an electron deficient olefin precursor and a source of aldehyde, in the presence of a catalyst comprising a lanthanide element or a transition element selected from niobium, zirconium or scandium, under appropriate conditions and for a time sufficient to yield an electron deficient olefin;
   (b) optionally, separating therefrom the so formed electron deficient olefin substantially free from the electron deficient olefin precursor, the source of aldehyde and/or the catalyst, and by-products.

3. The process of claim 2, wherein the electron deficient olefin precursor is an ester of cyanoacetic acid.

4. The process of claim 1, wherein the aldehyde compound is a member selected from the group consisting of paraformaldehyde, formalin, 1,3,5-trioxan, methylene diacetate, dimethoxymethane and acrolein.

5. A process for the preparation of a reactive electron deficient olefin, steps of which comprise:
   (a) reacting an electron deficient olefin precursor and a source of aldehyde, in the presence of a catalyst comprising a lanthanide element or a transition element, under appropriate conditions and for a time sufficient to yield an electron deficient olefin;

(b) optionally, separating therefrom the so formed electron deficient olefin substantially free from the electron deficient olefin precursor, the source of aldehyde and/or the catalyst, and by-products, wherein the electron deficient olefin is a biscyanoacrylate, biscyanopentadienoate, biscyanohexadienoate, or a bis-alkylene derived from dimalonates or malononitrile and combinations thereof.

6. The process of claim 1, wherein the electron deficient olefin is a compound having one end terminating with a cyanoacrylate, cyanopentadienoate, cyanohexadienoate, or alkylene derived from dimalonate and another end terminating with a group selected from the group consisting of branched and unbranched alkyl esters, esters containing aromatics and heterocylic nuclei, (meth)acrylates, cyanoacrylates, siloxanes, blocked and unblocked isocyanates, anhydrides, silanes, vinyls, acetylenes, and epoxies.

7. The process of claim 2, wherein the electron deficient olefin is a 2-cyanoacrylate.

8. The process of claim 7, wherein the 2-cyanoacrylate has as an ester group a member selected from the group consisting of methyl, ethyl, propyl, isoamyl, propargyl, butyl, pentyl, hexyl, octyl, nonyl, oxononyl, decyl, dodecyl, allyl, ethynyl, butenyl, cyclohexyl, phenyl, phenethyl, tetrahydrofurfuryl, chloroethyl, 2,2,2-trifluoroethyl, hexafluoroisopropyl, methoxymethyl, thiomethoxymethyl, methoxyethyl, thiomethoxyethyl, methoxybutyl, thiomethoxybutyl, ethoxyethyl, thioethoxyethyl, propoxyethyl, thioproxyethyl, butoxymethyl, thiobutoxymethyl, butoxyethyl, thiobutoxyethyl, and dimethylsiloxane esters of 2-cyanoacrylic acid.

9. The process of claim 1, wherein the catalyst comprising a lanthanide element or a transition element has one or more ligands bound to the element(s).

10. The process of claim 1, wherein the catalyst comprises ytterbium.

11. The process of claim 1, wherein the catalyst comprises niobium.

12. The process of claim 9, wherein the one or more ligands is selected from halogens, triflates, mesylates, nitrates or tosylates.

13. The process of claim 2, wherein the electron deficient olefin precursor is embraced by:

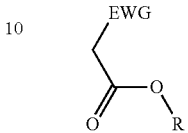

wherein EWG represents an electron withdrawing group selected from cyano or nitrile, alkoxy or aryloxy, carboxyl, sulphonic acids, carbonyls, halogens, nitro, isocyanate, sulfoxide and phosphine oxide; and R here represents straight chain, branched, cyclic or fused $C_{1-20}$ alkyl or alkylenyl, $C_{2-20}$ alkenyl or alkenylenyl, $C_{2-20}$ alkynyl or alkynylenyl, and $C_{6-20}$ aryl or arylenyl or $C_{7-20}$ alkaryl or alkarylenyl, with or without substitution or interruption by one or more heteroatoms.

14. The process of claim 2, wherein the aldehyde compound is a member selected from the group consisting of paraformaldehyde, formalin, 1,3,5-trioxan, methylene diacetate, dimethoxymethane and acrolein.

15. The process of claim 2, wherein the catalyst comprising a lanthanide element or a transition element has one or more ligands bound to the element(s).

16. The process of claim 2, wherein the catalyst comprises a lanthanide element.

17. The process of claim 2, wherein the catalyst comprises ytterbium.

18. The process of claim 2, wherein the catalyst comprises niobium.

* * * * *